(12) United States Patent
Bryhn et al.

(10) Patent No.: US 9,282,760 B2
(45) Date of Patent: Mar. 15, 2016

(54) USE OF A FATTY ACID COMPOSITION COMPRISING AT LEAST ONE OF EPA AND DHA OR ANY COMBINATIONS THEREOF

(75) Inventors: Morten Bryhn, Svelvik (NO); Jan Kopecky, Prague (RU)

(73) Assignee: PRONOVA BIOPHARMA NORGE AS, Baerum (NO)

( * ) Notice: Subject to any disclaimer, the term of this patent is extended or adjusted under 35 U.S.C. 154(b) by 287 days.

(21) Appl. No.: 10/582,978

(22) PCT Filed: Dec. 17, 2004

(86) PCT No.: PCT/IB2004/004178
§ 371 (c)(1),
(2), (4) Date: Jun. 15, 2006

(87) PCT Pub. No.: WO2005/060954
PCT Pub. Date: Jul. 7, 2005

(65) Prior Publication Data
US 2007/0112071 A1 May 17, 2007

Related U.S. Application Data

(60) Provisional application No. 60/530,644, filed on Dec. 19, 2003.

(30) Foreign Application Priority Data

Dec. 19, 2003 (SE) .................................. 030513-6

(51) Int. Cl.
*A61K 31/225* (2006.01)
*A23L 1/30* (2006.01)
(Continued)

(52) U.S. Cl.
CPC .............. *A23L 1/3008* (2013.01); *A23L 1/293* (2013.01); *A61K 31/202* (2013.01); *A61K 31/232* (2013.01); *A61K 31/557* (2013.01); *A61K 45/06* (2013.01); *A23V 2002/00* (2013.01)

(58) Field of Classification Search
CPC .. A61K 31/232; A61K 31/202; A61K 31/557
USPC ........................................................ 514/547
See application file for complete search history.

(56) References Cited

U.S. PATENT DOCUMENTS 5,013,569 A 5/1991 Rubin
5,502,077 A * 3/1996 Breivik et al. ................ 514/560
(Continued)

FOREIGN PATENT DOCUMENTS

CA 2 433 762 * 8/2002
JP 03-094655 4/1991
(Continued)

OTHER PUBLICATIONS

Jeffrey M. Zigman et al., In search of an effective obesity treatment: A shot in the dark or a shot in the arm?, PNAS | Aug. 29, 2006 | vol. 103 | No. 35 | 12961-12962, printed pp. 1-7, especially p. 3, 3rd paragraph.*

(Continued)

*Primary Examiner* — San-Ming Hui
(74) *Attorney, Agent, or Firm* — Finnegan, Henderson, Farabow, Garrett & Dunner, L.L.P.

(57) ABSTRACT

A method is disclosed for treatment and prevention of obesity, an overweight condition or for controlling body weight reduction, wherein an effective amount of a fatty acid composition comprising at least one of (all-Z omega-3)-5,8,11,14,17-eicosapentaenoic acid (EPA) and (all-Z omega-3)-4,7,10,13,16,19-docosahexaenoic acid (DHA) or any combinations thereof, is administered to a human or an animal. Additionally, a dietary product is disclosed, containing a fatty acid composition comprising at least one of EPA and DHA or any combinations thereof, for non-medical treatment of obesity, an overweight condition and/or for supporting and controlling body weight reduction. Finally, a method is disclosed for supplementing a dietary product with a fatty acid composition mentioned above.

19 Claims, 9 Drawing Sheets

Composition of the semisyntetic high-fat diets (20 % w/w fat) containing flaxseed oil (Ln) and flaxseed oil with EPAX 2050TG; FO (Ln+FO)

Total body weight after one month of treatment. Lard (L), Lard plus EPAX2050TG (L+FO), Flaxseed oil (Ln) and Flaxseed plus EPAX2050TG (Ln+FO)

(51) Int. Cl.
*A23L 1/29* (2006.01)
*A61K 31/202* (2006.01)
*A61K 31/232* (2006.01)
*A61K 31/557* (2006.01)
*A61K 45/06* (2006.01)

(56) References Cited

U.S. PATENT DOCUMENTS

| | | | |
|---|---|---|---|
| 5,656,667 A | 8/1997 | Breivik et al. | |
| 5,962,062 A * | 10/1999 | Carrie et al. | 426/585 |
| 6,596,302 B2 * | 7/2003 | O'Connor et al. | 424/439 |
| 2003/0203004 A1 | 10/2003 | Kelm et al. | |
| 2005/0019372 A1 * | 1/2005 | Corkey et al. | 424/439 |

FOREIGN PATENT DOCUMENTS

| | | |
|---|---|---|
| JP | 04-273817 | 9/1992 |
| JP | 04300826 | 10/1992 |
| JP | 06-116585 | 4/1994 |
| JP | 3098560 | 4/1995 |
| JP | 11-209785 | 8/1999 |
| JP | 11-209786 | 8/1999 |
| JP | 2002-180082 | 6/2002 |
| JP | 2002315535 | 10/2002 |
| WO | WO 99/29316 | 6/1999 |
| WO | WO 2004018598 | 3/2004 |
| WO | WO 2004/012727 | 12/2004 |

OTHER PUBLICATIONS

Kenchaiah et al., New England Journal of Medicine, 2002;347(5):305-313.*

Cunnane et al., British Journal of Nutrition, 1986;56(1):87-95.*

Awad et al. "Effect of Sterols and Fatty Acids on Growth and Triglyceride Accumulation In 3T3-L1 Cells" J. Nutr. Biochem., ©2000, vol. 11, Mar.

Cha et al., "Effect of fish Oils with EPA, DHA on Lipid Metabolism and Adipose Tissue in KK-A Mice," (1999), *Journal of Kagawa Nutrition University*, vol. 30, pp. 35-44.

Uenishi et al., "Anti-obesity Effect of Soy Milk Containing Docosahexaenoic Acid in young Japanese Adult Women," (2002), *Journal of the Japan Society of Nutrition and Food Science*, vol. 55(6), pp. 339-345.

Ikemoto et al., "High-fat diet-induced hyperglycemia and obesity in mice: Differential effects of dietary oils," *Metabolism* (1996), vol. 45, pp. 1539-1546.

Nordic Naturals, Nordic Naturals Ultimate Omega DHA Formula Supports Brain & Nervous System Function [online], Aug. 8, 2002, retrieved May 25, 2007 from http://web.archive.org/web/20020808004616/www.nordicnaturals.com/consumer/products_dha.html.

Nordic Naturals, Nordic Naturals Ultimate Omega EPA Formula Product Specification Supports Cardiovascular Health [online], Aug. 8, 2002, retrieved May 25, 2007 from http://web.archive.org/web/20020808004344/www.nordicnaturals.com/consumer/products_epa.html.

http://www.epax.com/Products/.

Ezaki, Osamu, "Mechanism of prevention of lifestyle related diseases by fish oil intake" Pharmacia, No. 35, vol. 11, pp. 1146-1150 (1999).

Third Party Observation submitted in Japanese Application No. 2006-544592, dated May 29, 2009.

EP Communication dated Jan. 22, 2010, in Application No. 04 806 374.7-2123.

EP Communication dated Jan. 27, 2011, in Application No. 04 806 374.7-2123.

EP Communication dated Feb. 2, 2011, in Application No. 10 183 626.0-2123.

EP Communication dated Jan. 11, 2012, in Application No. 10 183 626.0-2123.

Ackman et al., Omega-3 Fatty Acids, ACS Symposium Series, vol. 788, pp. 191-207, Mar. 27, 2001 (abstract).

Bao et al, Effects of Dietary Fish and Weight Reduction on Ambulatory Blood Pressure in Overweight Hypertensives, 32: 710-717, 1998.

Chan et. al, Factorial study of the effects of atorvastatin and fish oil on dyslipidaemia in visceral obesity, European Journal of Clinical Investigation 32, 429-436, 2002.

Chan et. al, Randomized controlled trial of the effect of n-3 fatty acid supplementation on the metabolism of apolipoprotein B-1 00 and chylomicron remnants in men with visceral obesity, Am. J. Clin. Nutr. 77:300-7, 2003.

Mori et. al, Docosahexaenoic Acid but Not Eicosapentaenoic Acid Lowers Ambulatory Blood Pressure and Heart Rate in Humans, Hypertension, 34:253-260, 1999.

Mori, et. al, Effects of varying dietary fat, fish, and fish oils on blood lipids in a randomized controlled trial in men at risk of heart disease, Am. J. Clin. Nutr. 59:1060-8, 1994.

Oudart et. al, Brown fat thermogenesis in rats fed high-fat diets enriched with n-3 polyunsaturated fatty Acids, International Journal of Obesity, 21, 955-962, 1997.

Stark et. al, Effect of a fish-oil concentrate on serum lipids in postmenopausal women receiving and not receiving hormone replacement therapy in a placebo-controlled, double-blind trial, Am. J. Clin. Nutr. 72:389-94, 2000.

* cited by examiner

Composition of the semisyntetic high-fat diets (20 % w/w fat) containing flaxseed oil (Ln) and flaxseed oil with EPAX 2050TG; FO (Ln+FO)

Total body weight after one month of treatment. Lard (L), Lard plus EPAX2050TG (L+FO), Flaxseed oil (Ln) and Flaxseed plus EPAX2050TG (Ln+FO)

Composition of semisynthetic high-fat diets (20 % w/w fat) containing flaxseed oil (Ln), flaxseed oil with a higher dose of EPAX2050TG (Ln+FO) and flaxseed oil with a lower dose of EPAX2050TG (Ln+FO Low)

Total body weight after two months of treatment. Flaxseed oil (Ln), Flaxseed oil plus a higher dose of EPAX2050TG (Ln+FO) and Flaxseed oil plus a lower dose of EPAX2050TG (Ln+FO Low).

Composition of semi synthetic high-fat (20 % w/w fat) diets containing Flaxseed oil (Ln), Corn oil (K), EPAX 1050TG (high in DHA) (D), EPAX 4510TG (high in EPA) (E), Corn oil + EPAX 1050TG (K+D), and Corn oil + EPAX 4510TG (K+E).

Composition of standard diet (ST) and semisyntetic diet.

Food consumption per day and animal during 8 weeks.

Total body weight after two months of treatment compared to a control group (ST). Flaxseed oil (Ln), Corn oil (K), Corn oil + EPAX 1050TG (K+D), and Corn oil + EPAX 4510TG (K+E).

Energy content of a standard chow diet (ST), a regular HF (high fat) diet, and a semisynthetic HF diet.

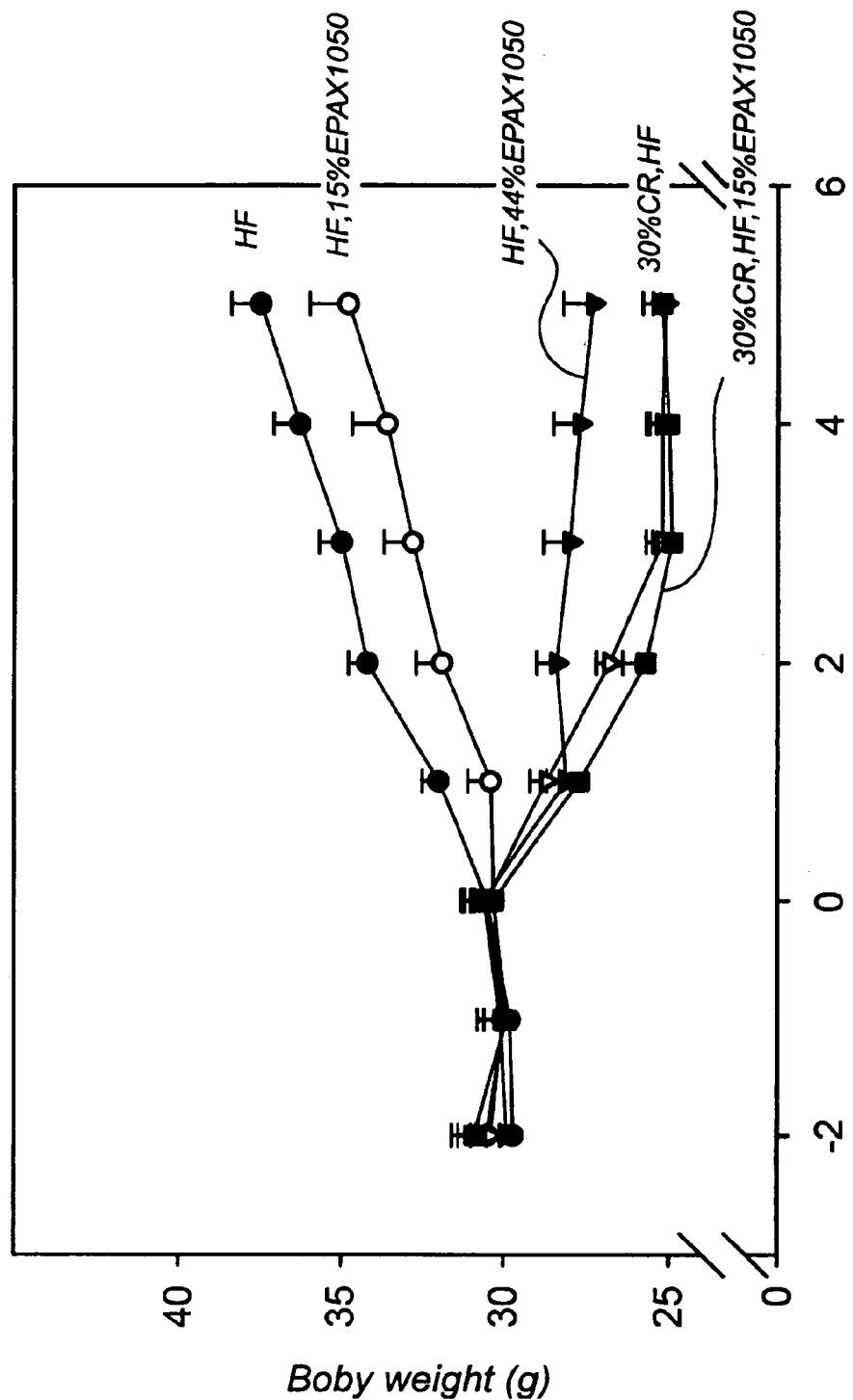

Change of body weight during 5 weeks of treatment. Regular HF diet ad libitum (-FO), regular HF diet where EPAX 1050 TG formed 15 % w/w (low dose) of the content of the diet (+FO low) and regular HF diet where EPAX 1050 TG formed 44 % w/w (low dose) of the content of the diet (+FO).

*Effects of EPAX1050TG and 10% CR on body weight.*

USE OF A FATTY ACID COMPOSITION COMPRISING AT LEAST ONE OF EPA AND DHA OR ANY COMBINATIONS THEREOF

This application is a national stage filing under 35 U.S.C. §371 of International Application No. PCT/IB04/04178, filed on Dec. 17, 2004, which claims priority of U.S. Provisional Patent Application No. 60/530,644 and Swedish Application No. 030613-6, both filed on Dec. 19, 2003. The contents of these applications are each incorporated herein by reference.

TECHNICAL FIELD OF THE INVENTION

The present invention comprises a number of aspects. According to the first aspect of the present invention, a use of a new medical product for controlling body weight reduction, for preventing body weight gain and for treatment and/or prevention of obesity or an overweight condition is disclosed. According to a second aspect of the present invention, a method for treatment and/or prevention of obesity, an overweight condition or for controlling body weight reduction, is disclosed. According to a third aspect of the invention, a use of a food stuff or food supplement for controlling and supporting body weight reduction and/or for prevention of body weight gain in a human or an animal, is disclosed. Moreover, according to a fourth aspect of the present invention, a dietary product for non-medical treatment of obesity, an overweight condition and/or for supporting and controlling weight reduction and/or for prevention of body weight gain, is disclosed. Additionally, according to a fifth aspect of the present invention, a use of a dietary food stuff or food supplement for controlling and supporting weight reduction and/or for prevention of weight gain, is disclosed. Finally, according to the sixth aspect of the present invention, a method for supplementing a dietary food stuff, is disclosed. The aspects above are based on at least one of the following features: a fatty acid composition comprising at least one of (all-Z omega-3)-5,8,11,14,17-eicosapentaenoic acid (EPA), or derivatives thereof, and (all-Z omega-3)-4,7,10,13,16,19-docosahexaenoic acid (DHA), or derivatives thereof, or any combinations thereof, or a step of adding a fatty acid composition comprising at least one of EPA and DHA or any combinations thereof, to a supplement product.

BACKGROUND ART

More individuals are becoming overweight and obese, a condition now considered to be the most common nutritional disorder in the industrialized world today. Overweight and obesity can be defined by a body-mass index exceeding 25 or 30. Normal values range from 18 to 25. In the US 34% of the population is overweight and another 27% is obese. This means that more than 60% of the entire population in the US has what can be defined as having a weight problem, which is likely to cause severe health problems, such as hypertension and elevated blood lipids, all risk factors for cardiovascular disease.

Overweight and obesity are caused by an imbalance between energy intake and energy use. In the industrialized world we tend to eat too much and engage in physical activities too little. However, the likelihood of becoming fat under these conditions is not the same for everyone, as witnessed by the fact that slim individuals exist under the same conditions as those who are overweight. Furthermore, the revelation that nutritional factors may control gene expression has opened up the possibility of developing novel therapeutic alternatives to treat obesity. The major problem in therapeutic strategies aimed to treat obesity and decrease body fat deposit is that such strategies act against potent and multiple mechanisms evolved in order to store metabolic energy and support survival under the periods when nutrition is scarce.

Once stored in adipose tissue, the metabolic energy is only released under the conditions of high food intake negative energy balance, namely during fasting and/or physical exercise. Importantly, the loss of the energy content of the tissue under these conditions results from both, increased secretion of fatty acids from adipose tissue cells, and catabolism of tissue lipids, which increases during fasting (Wang T et al., Obesity Research 11:880-887, 2003).

Fats are composed of fatty acids and fat is the most calorie dense nutrient. High fat diets are linked to excess weight gain, but not all fats are equal. In the gastrointestinal tract fats are broken down into fatty acids by lipases and absorbed into the intestinal cells. In intestinal cells, the lymphatic system and the liver, fatty complexes are produced to transport fatty acids. In the circulation these fatty acids are released by lipases entering cells or getting integrated into the cell membranes. Most fatty acids are used for energy, but some, especially polyunsaturated fatty acids have other functions including interacting with cellular proteins, which in turn enter the nucleus and turn genes off and on. These genes are known to encode proteins important in controlling energy production from glucose and fat.

Fatty acids differ in their three-dimensional structure, which is determined by the chain-length of the molecule and the number of double bonds present. The most common dietary fats are medium to long chains fatty acids. Saturated fatty acids have no double bonds, resulting in a straight molecule. If a double bond is present then an angle of 120 degrees is produced. Thus, polyunsaturated fatty acids (PUFA's) have a completely different spatial resolution when compared to the saturated fatty acids. The differences in three dimensional structure between fatty acids means that while the PUFA's can act as signalling agents to the cell, switching gene transcription off or on, the saturated fatty acids are not recognised and have no effect. In the laboratory calorimeter all fats irrespective of their saturated or unsaturated nature generate 9 kcal of energy per gram, but when part of the diet, PUFA's give completely different net effects on metabolic energy production and weight gain compared to the saturated fatty acids. Thus, saturated fatty acids are the main source of energy in the human body, while PUFAs fulfil a different function. PUFA's are derived mainly from seeds, nuts or fish oil. They may have their first double bond located either three, six or nine carbon atoms away from the chain end. Thus, they are known either as omega-3, omega-6 and omega-9 fatty acids, or n-3, n-6 and n-9 fatty acids. Humans can not synthesise fatty acids with double bonds at the 3 or 6 location making these fatty acids essential dietary components. In certain cases both types of PUFA's may have the same action. One example is the effects of PUFA's on suppressing lipid synthesis in the liver while at the same time up-regulating fatty acid oxidation in the liver and skeletal muscle. It has also been demonstrated that PUFA's decrease the transcription of hepatic genes encoding glycolytic and lipogenic enzymes. The effect of the PUFA's on gene expression in the liver and muscle thus leads to increased metabolism and decreased fat storage, helping to prevent weight gain. Energy conversion is mainly located to the mitochondria within the cell. The mitochondria preferentially oxidise medium- and short-chain fatty acids. Energy released is converted into ATP, which is used for a large number of energy dependent processes. However, mitochondrial energy conversion is not 100% efficient, and part of the metabolic energy is released as heat. The efficiency of mitochondrial energy conversion is modulated by mitochondrial uncoupling proteins. Further, the PUFA's also affect another site for metabolic energy conversion, namely the peroxisome also located inside the cell membrane. While the main role of mitochondria is the production of the energy-rich ATP, peroxisomes are more active in the generation of heat, while shortening polyunsaturated long-chain fatty acids before their further oxidation in mitochondria. The net effect is increased production of heat instead of increasing the fat deposits. PUFA's are peroxisome proliferators increasing the amount and the activity of peroxisomes.

Moreover, during fasting, a major physiological situation leading to the depression of adiposity, energy content of fat cells may be reduced by several mechanisms, like upregulation of mitochondrial uncoupling protein 2, see (Millet L et al. J. Clin. Invest. 100:2665-2670, 1997; Vidal-Puig A. et al. Obesity Research 7:133-140, 1999). Moreover, it has been shown that reduction of abdominal fat by dietary omega-3 PUFAs in rats is associated with increased levels of expression of uncoupling proteins 2 and 3 in adipose tissue (Oudart H. et al. Int. J. Obesity and Metab. Disord. 24 Supp 1:S130, 2000; Hun C. S. et al. Biochem. Biophys. Res. Commun. 259:85-90, 1999) Furthermore, it has also been shown that a 6 g/day substitution of visible fat by fish oil in healthy adults reduces fat mass and increases basal lipid oxidation (Couet C, Delarue J, Ritz P, Antoine J-M and Lamisse F, 1997, International Journal of Obesity 21: 637-643), but at the same time the fish oil had no significant effect on body weight reduction. Finally, US 2003203004 A1 descibes a composition comprising short and long chain fatty acids which are useful for the management of body weight.

SUMMARY OF THE INVENTION

Based on the present invention a number of aspects are presented in the appended claims. These aspects are;
1. Use of a new medical product for controlling body weight reduction, for prevention of body weight gain and/or for treatment and/or prevention of obesity or an overweight condition.
2. A method for treatment and/or prevention of obesity, an overweight condition or for controlling body weight reduction and/or prevention of body weight gain.
3. Use of a food stuff or food supplement for controlling and supporting body weight reduction and/or prevention of body weight gain in a human or an animal.
4. A dietary product for non-medical treatment and/or prevention of obesity, an overweight condition and/or for supporting and controlling weight reduction and/or for inhibiting body weight gain.
5. Use of a dietary food stuff or food supplement for controlling and supporting weight reduction and/or for preventing body weight gain.
6. A method for supplementing a dietary food stuff.

The aspects above are based on at least one of the following features:
  a fatty acid composition comprising at least one of (all-Z omega-3)-5,8,11,14,17-eicosapentaenoic acid (EPA), or derivatives thereof, and (all-Z omega-3)-4,7,10,13,16,19-docosahexaenoic acid (DHA), or derivatives thereof, or any combinations thereof.
  a step of adding a fatty acid composition comprising at least one of (all-Z omega-3)-5,8,11,14,17-eicosapentaenoic acid (EPA), or derivatives thereof, and (all-Z omega-3)-4,7,10,13,16,19-docosahexaenoic acid (DHA), or derivatives thereof, or any combinations thereof, to the supplement product.

According to a first aspect of the invention, the invention relates to the use of a fatty acid composition comprising at least one of (all-Z omega-3)-5,8,11,14,17-eicosapentaenoic acid (EPA), or derivatives thereof, and (all-Z omega-3)-4,7,10,13,16,19-docosahexaenoic acid (DHA), or derivatives thereof, or any combinations thereof, for the production of a medicinal product for controlling body weight reduction, for treatment and/or prevention of obesity or an overweight condition and/or for prevention of body weight gain. From research leading to the invention it was surprisingly found that a fatty acid composition according to the invention leads to body weight reduction in mice and prevents body weight gain in mice fed a high fat (HF) diet, so called HF obesity-promoting diet.

In a preferred embodiment, the invention relates to the use of a fatty acid composition comprising (all-Z omega-3)-4,7,10,13,16,19-docosahexaenoic acid (DHA), or derivatives thereof, or a combination of (all-Z omega-3)-5,8,11,14,17-eicosapentaenoic acid (EPA) and (all-Z omega-3)-4,7,10,13,16,19-docosahexaenoic acid (DHA), or derivatives thereof, wherein the weight ratio of EPA:DHA in the fatty acid composition is 1:X, where X is equal or greater than 1, for the production of a medicinal product for controlling body weight reduction, treatment and/or prevention of obesity or an overweight condition and/or for prevention of body weight gain. Please note that X being one of an integer or non-integer.

Moreover, from the research leading to the invention it was found that the most preferred effect of the invention concerning weight reduction is accomplished by a fatty acid composition rich in DHA. The term "rich" herein includes more or less a fatty acid composition primary containing DHA (none EPA), or derivatives thereof, and a fatty acid composition where the amount of DHA≥EPA. Further, the term "amount" herein relates to weight or volume of the fatty acid composition. Moreover, the desired pharmacological and/or therapeutic effect may be achieved by the fatty acid composition according to the invention.

In addition, as known before, food reduction alone will not effectively lead to weight reduction in a human. Suitably, the treatment according to the invention is combined with at least one of calorie restriction, (fasting), dietary and physical exercise or combinations thereof, that may lead to body weight reduction and/or inhibiting of body weight gain in a human or an animal. Preferably, the dietary, i.e. the reduction of calories, is designed in order to make an animal or a human more sensitive to the effect of a fatty acid composition according to the invention.

Furthermore, this opens up for a future market for a pharmaceutical, a food stuff and/or a dietary product containing the fatty acid composition according to the invention not only for the purpose of treating and/or preventing obesity or overweight conditions, but also for the purpose of controlling and supporting body weight reduction (a helping hand for weight control, body weight reduction, preferably in combination with a reduced intake of calories) and prevention of body weight gain, preferably under development of obesity or an overweight condition.

In a preferred embodiment of the invention, EPA and DHA, or derivatives thereof, in the fatty acid composition are present in the composition in an EPA:DHA ratio from 1:1 to 1:8. In a more preferred embodiment the EPA:DHA ratio in the fatty acid composition is from about 1:1 to 1:6. Moreover, the invention also includes administering a fatty acid composition that is a DHA-product or a DHA-derivative product.

In another embodiment, the fatty acids in the composition according to the invention is presented in at least one of esterified form, ethyl ester form, salt form and free acid form, or any combinations thereof. In a preferred embodiment, the fatty acid composition is comprised of a combination of EPA and DHA, or derivatives thereof, in triglyceride form.

In another embodiment, at least one of EPA and DHA is obtained from at least one of vegetable, microbial and animal origins or combinations thereof. The invention includes therefore for instance a fatty acid composition comprising at least one of a DHA-containing microbial oil and a mixture of an DHA-containing oil from microbial origin and a EPA-containing oil from a marine origin. Further, the fatty acid composition according to the invention may additionally also comprise at least one of arachidonic acid (ARA), docosapentaenoic acid, heneicosapentaenoic acid and octadecatentraenoic or derivatives thereof, or any combinations thereof. Suitably, at least a part of the EPA and/or DHA, or derivatives thereof, is produced from a marine oil, preferably a fish oil. Furthermore, in another embodiment the fatty acid composition is produced from a marine oil, such as a fish oil.

Moreover, it should be pointed out that the fatty acid composition is administered to a human or an animal, preferably orally, in the form of for instance a pill or a soft capsule. However, the medicinal product according to the invention may also be produced for administration though any other route where the active ingredients may be efficiently absorbed and utilized, e.g. intravenously, subcutaneously or intramuscularly.

In a preferred embodiment of the invention the treatment or intake of a medicinal product is carried out together with a reduced intake of calories for a human or an animal. Suitably, the reduced intake of calories is also combined with physical exercise. If the administration of a medicinal product according to the invention, to a human or an animal, goes hand-in-hand with a reduced intake of calories the reduction in body weight will be more effective. Moreover, the above also leads to prevention of body weight gain in overweight or obese human or animals.

In a preferred embodiment of the invention, the treatment with a fatty acid composition is combined with at least 5% calorie restriction. Preferably, the treatment with a fatty acid composition is combined with a calorie restriction in the interval 10-15%.

In another preferred embodiment of the invention, the fatty acid composition comprising at least one of EPA and DHA, derivatives thereof, or any combination thereof is administered in a daily dosage in the interval 10-40% of the total lipid content of a daily diet for a human or an animal. This means that 10 up to 40% of the total lipid content of a daily diet may be replaced by the fatty acid composition according to the invention. Please note that, another way of defining the daily dosage of the fatty acid composition is presented above.

In another preferred embodiment of the invention, the fatty acid composition comprising DHA, or derivatives thereof, or a combination of EPA and DHA is administered in an amount providing a daily dosage of 1 g to 15 g of said fatty acid composition. In a more preferred embodiment between 2 and 10 g of said fatty acid composition is administered per day, and in a most preferred embodiment between 2 and 8 g of said fatty acid (per day). As has been shown in the experiments the effect of the fatty acid composition according to the invention seams to be extra strong at high doses. The medicinal product or pharmaceutical composition or pharmaceutical preparation according to the invention may also comprise other substances such as an inert vehicle, or pharmaceutical acceptable adjuvants, carriers, preservatives etc., which are well known in to those skilled in the art. The fatty acid composition according to the invention may also be administered in a liquid form. Additionally, the medicinal product may be administered to an animal such as a pet or a horse.

According to a second aspect of the invention, the invention relates to a method for treatment and/or prevention of obesity, and overweight condition or for controlling body weight reduction and/or prevention of body weight gain, wherein an effective amount of a fatty acid composition comprising at least one of (all-Z omega-3)-5,8,11,14,17-eicosapentaenoic acid (EPA) or derivatives thereof, and (all-Z omega-3)-4,7,10,13,16,19-docosahexaenoic acid (DHA), or derivatives thereof, or combinations thereof, is administered to a human or an animal. Herein, "an effective amount" also includes a therapeutically or a pharmaceutically active amount of the fatty acid composition. This expression relates to a dose of said fatty acid composition that will lead to the desired pharmacological and/or therapeutic effect. The desired pharmacological and/or therapeutic effect is, as stated above, achieved by the fatty acid composition according to the invention.

In a preferred embodiment of the method, said fatty acid composition comprising DHA, derivatives thereof, or a combination of EPA and DHA, wherein the weight ratio of EPA:DHA in the fatty acid composition is 1:X, where X is equal or greater than 1. This method leads to the same advantages and possibilities as mentioned before. Thus, the embodiments described above is also included for the method according to the invention concerning treatment and/or prevention of obesity, an overweight condition and/or for controlling and/or reducing body weight and also for prevention of body weight gain, preferably in overweight or obese humans or animals. Additionally, in another embodiment of the method according to the invention, with the aim to reduce body weight, said fatty acid composition is administered in a daily dosage that corresponds to at least 10% of the total lipid content of a daily diet for a human or an animal.

According to a third aspect of the invention, the present invention relates to the use of a fatty acid composition comprising at least one of (all-Z omega-3)-5,8,11,14,17-eicosapentaenoic acid (EPA), derivatives thereof, and (all-Z omega-3)-4,7,10,13,16,19-docosahexaenoic acid (DHA), derivatives thereof, or any combinations thereof, for the production of a food stuff or food supplement for controlling and supporting body weight reduction and/or for prevention of body weight gain. From research leading to the invention it was surprisingly found that a fatty acid composition according to the invention leads to a body weight reduction in mice and prevents body weight gain in mice fed a high fat (HF) diet, so called HF obesity-promoting diet.

In a specific embodiment, the present invention relates to the use of a fatty acid composition comprising (all-Z omega-3)-4,7,10,13,16,19-docosahexaenoic acid (DHA), derivatives thereof, or a combination of (all-Z omega-3)-5,8,11,14,17-eicosapentaenoic acid (EPA), derivatives thereof, and (all-Z omega-3)-4,7,10,13,16,19-docosahexaenoic acid (DHA), or derivatives thereof, wherein the weight ratio of EPA:DHA in the fatty acid composition is 1:X, where X is equal or greater than 1, for the production of a food stuff or food supplement for controlling body weight and for supporting weight reduction and/or for inhibiting or slowing down body weight gain. The most preferred effect of the invention related to body weight reduction is also there accomplished by the use of DHA, derivatives thereof, or a fatty acid composition rich in DHA, i.e. more DHA in relation to EPA. One advantage of manufacturing and selling a food stuff for at least one of reducing body weight, controlling and supporting body weight reduction and/or prevention of body weight gain is that such a food stuff will be more easily accessible for people. They preferably buy the product or supplement in a health store and/or a supermarket, and they do not need to visit a doctor.

In a preferred embodiment of the invention, EPA and DHA, or derivatives thereof, in the fatty acid composition are present in the composition in an EPA:DHA ratio from 1:1 to 1:8. In a more preferred embodiment the EPA:DHA ratio in the fatty acid composition is from about 1:1 to 1:6. In another embodiment of the invention, the fatty acid composition is a DHA-product, or a DHA-derivative product.

Moreover, in another embodiment, the fatty acids in the composition according to the invention is presented in at least one of esterified form, ethyl ester form, salt form and free acid form, or any combinations thereof. In a preferred embodiment, the fatty acid composition is comprised of a combination of EPA and DHA in triglyceride form.

In another embodiment, at least one of EPA and DHA is obtained from at least one of vegetable, microbial and animal origins. The food stuff or food supplement includes therefore for instance a fatty acid composition comprising at least one of a DHA-containing microbial oil and a mixture of an DHA-containing oil from microbial origin and a EPA-containing oil from a marine origin. Further, the fatty acid composition according to the invention may additionally also comprise other fatty acids as mentioned before. Suitably, at least a part of the EPA and/or DHA is produced from a marine oil, preferably a fish oil.

Furthermore, in another embodiment of the food stuff or food supplement the fatty acid composition is produced from a marine oil, such as a fish oil. Moreover, it should be pointed out that the fatty acid composition is administered to a human or an animal, preferably orally. However, the food stuff or food supplement according to the invention may also be produced for administration though any other route where the active ingredients may be efficiently absorbed and utilized, e.g. intravenously, subcutaneously, intramuscularly, intranasally, rectally, vaginally or topically. The fatty acid composition may also be part of an emulsion containing at least a liquid oil, and the food stuff or food supplement is administered as a liquid nutritional or as a beverage.

In a preferred embodiment of the invention, the intake of a food stuff or food supplement is carried out together with a reduced intake of calories for a human or an animal. Herein an animal is a pet or a horse. Suitably, the reduced intake of calories is also combined with physical exercise. If the administration of a food stuff or food supplement according to the invention, to a human or an animal, goes hand-in-hand with a reduced intake of calories the reduction in body weight will be more effective. Moreover, in another embodiment for prevention of body weight gain, the intake of a food stuff or food supplement is carried out together with a reduced intake of calories for a human or an animal. A mild calorie restriction, preferably a reduction of between 5 and 20% of the calories in the daily diet, and the administration of a fatty acid composition according to the invention, seem to have an additive effect concerning prevention of body weight gain. Thus, in a preferred embodiment of the invention, the treatment with a fatty acid composition is combined with at least 5% calorie restriction. In a more preferred embodiment, the treatment with a fatty acid composition is combined with a calorie restriction in the interval 10-15%. In the light of the above, it may be possible to meet the definition of persistent weight reduction by FDA, which is 10% reduction over one year. From research leading to the invention it was surprisingly found that a combination of about 10% calorie restriction, and the treatment with a fatty acid composition according to the invention prevents body weight gain in obese animals.

In another preferred embodiment of the invention, said fatty acid composition is administered in a daily dosage in the interval 10-40% of the total lipid content of a daily diet for a human or an animal. This means that 10 up to 40% of the total lipid content of a daily diet may be replaced by the fatty acid composition according to the invention.

In another preferred embodiment of the invention, the fatty acid composition comprising DHA or a combination of EPA and DHA is administered in an amount providing a daily dosage of 1 g to 15 g of said fatty acid composition. In a more preferred embodiment between 2 and 10 g of said fatty acid composition is administered per day, and in a most preferred embodiment between 2 and 6 g of said fatty acid (per day). As mentioned before the effect of the fatty acid composition according to the invention seem to be extra strong at high doses, prefer-ably concerning weight reduction. Moreover, please note that treatment of overweight or obese animals or humans with a fatty acid composition according to the invention in low doses leads to inhibition or prevention of weight gain.

In another preferred embodiment, the food stuff or food supplement is in form of capsule, preferably a gelatine capsule which capsule is flavoured. This embodiment also includes a capsule, wherein both the capsule and the encapsulated fatty acid composition, preferably a fish oil, is flavoured. By flavouring the capsule as above, the product will become more attractive to the user.

Further, human beings are not designed to lose body weight only during fasting. A sound strategy for losing weight should also take into account measures of energy expenditure and dietary advice based on the individual.

Thus, according to a fourth aspect of the invention, the present invention relates to a dietary product containing a fatty acid composition comprising at least one of (all-Z omega-3)-5,8,11,14,17-eicosapentaenoic acid (EPA), derivatives thereof, and (all-Z omega-3)-4,7,10,13,16,19-docosahexaenoic acid (DHA), derivatives thereof, or any combinations thereof, for non-medical treatment and/or prevention of obesity, an overweight condition and/or for supporting and controlling body weight reduction and/or prevention of body weight gain.

In a preferred embodiment of the invention, the dietary product containing a fatty acid composition comprising (all-Z omega-3)-4,7,10,13,16,19-docosahexaenoic acid (DHA), or derivatives thereof, or a combination of (all-Z omega-3)-5,8, 11,14,17-eicosapentaenoic acid (EPA) and (all-Z omega-3)-4,7,10,13,16,19-docosahexaenoic acid (DHA), wherein the weight ratio of EPA:DHA in the fatty acid composition is 1:X, where X is equal or greater than 1, for non-medical treatment and/or prevention of obesity, an overweight condition and/or for supporting and controlling body weight reduction and/or for inhibiting body weight gain. Preferably, the main active ingredient in the fatty acid composition is DHA, or derivatives thereof.

In another embodiment of the invention, the dietary product is a weight-watching product or a slimming product.

In another embodiment according to the dietary product, the combination of EPA and DHA, or derivatives thereof, are present in the composition in an EPA:DHA ratio from about 1:1 to 1:8, preferably in an EPA:DHA ratio from 1:1 to 1:6.

In another embodiment of the dietary product, at least one of EPA and DHA is obtained from at least one of vegetable, microbial and animal origins or combinations thereof. Preferably, the fatty acid composition is produced from a marine oil, for instance a fish oil. Suitably, the intake of the dietary product is combined with a reduced intake of calories for a human and/or together with physical activity in order to accelerate and increase the weight reduction effect.

In a preferred embodiment of the dietary product, said fatty acid composition is administered in a daily dosage that corresponds to at least 10% of the total lipid content of a daily diet for a human or an animal.

Moreover, the dietary product may be a bar, snacks, or for instance a beverage, containing the fatty acid composition according to the invention.

According to a fifth aspect of the invention, the present invention relates to the use of a fatty acid composition comprising at least one of EPA, or derivatives thereof, and DHA, or derivatives thereof, or any combinations thereof, in the manufacture of a dietary product for controlling and supporting weight reduction and/or for preventing body weight gain in a human.

In a preferred embodiment, the use of a fatty acid composition comprising (all-Z omega-3)-4,7,10,13,16,19-docosahexaenoic acid (DHA), or derivatives thereof, or a combination of (all-Z omega-3)-5,8,11,14,17-eicosapentaenoic acid (EPA) and (all-Z omega-3)-4,7,10,13,16,19-docosahexaenoic acid (DHA), wherein the weight ratio of EPA:DHA in the fatty acid composition is 1:X, where X is equal or lager than 1, in the manufacture of a dietary product for preventing of body weight gain and/or for controlling body weight and for supporting weight reduction in a human. Moreover, from the research leading to the invention, the most preferred effect of the invention concerning both weight reduction and prevention of weight gain are accomplished by a fatty acid composition rich in DHA. One specific use of the fatty acid composition according to the invention is to incorporate the fatty acid composition in a supplement product.

According to a sixth aspect of the invention, the invention relates to a method for supplementing a dietary product comprising the step of adding a fatty acid composition comprising at least one of EPA, or derivatives thereof, and DHA, or derivatives thereof, or any combinations thereof, to a the supplement product for controlling and supporting weight reduction and/or for prevention of body weight gain, preferably in a human.

In a preferred embodiment of the method for supplementing a dietary product, the invention relates to the step of adding a fatty acid composition comprising (all-Z omega-3)-4,7,10,13,16,19-docosahexaenoic acid (DHA), or derivatives thereof, or a combination of (all-Z omega-3)-5,8,11,14,17-eicosapentaenoic acid (EPA) and (all-Z omega-3)-4,7,10,13,16,19-docosahexaenoic acid (DHA), or derivatives thereof, wherein the weight ratio of EPA:DHA in the fatty acid composition is 1:X, where X is equal or lager than 1, to a supplement product, such as a weight-watching product or a slimming product.

Most of the dietary products on the market containing small amounts of saturated fatty acids. The invention opens up for possibilities to incorporated the fatty acid composition according to the invention in a new or already existing dietary product. In a preferred embodiment of the invention an fish oil is incorporated in a dietary product. Thus, this may be a faster way to reach the market with a dietary product, which product has the aim of supporting, controlling and/or trigger body weight reduction. Moreover, a body weight controlling agent containing an effective amount of a fatty acid composition, wherein the main active ingredients are at least one of (all-Z omega-3)-5,8,11,14,17-eicosapentaenoic acid (EPA), or derivatives thereof, and (all-Z omega-3)-4,7,10,13,16,19-docosahexaenoic acid (DHA), or derivatives thereof, or any combinations thereof, for treatment and/or prevention of body weight reduction or for inhibiting body weight gain is also included herein.

Moreover, obesity, having an excessive amount of body fat, is herein defined as a body mass index over 30, wherever overweight is defined as a body mass index exceeding 25. Obesity also includes visceral or general obesity that is due to genetic predisposition, sometimes described as the thrifty genotype. Obesity caused by life cycle and environment, such as diets with high fat content or a high calorie content, or lack of exercise, can also be treated as described herein. As used herein the term "treatment" means both treatment having a curving or alleviating purpose and the treatment of obesity or an overweight condition can be made either acutely or chronically. By chronically treatment is meant treatment that continues for more than some weeks or years. Moreover, the present invention also includes preventing body weight gain by administering a fatty acid composition according to the invention. As used herein, the term prevention of body weight gain also means inhibiting body weight gain and effecting or controlling weight loss.

BRIEF DESCRIPTION OF THE DRAWINGS

In the studies and examples below reference is made to the accompanying drawings, where all figures concern studies performed on mice. The studies were preformed in order to demonstrate that a treatment with a fatty acid composition comprising at least one of EPA and DHA or any combinations thereof, reduces body weight and/or under some conditions also prevents body weight gain. Herein reference is made to the accompanying drawings, on which:

FIG. 5B illustrates weight reduction and prevention of gain in body weight in mice fed ad libitum HF composite diet, either with no further modification (full circles), or with replacement of 15% (empty circles) or 44% (full triangles) of its fat content by EPAX 1050TG (rich in DHA), or mice on the calorie restriction (CR) regime fed either the HF composite diet alone (empty triangles) or the diet, in which 15% of the lipids in the diet was formed by EPAX 1050TG (full squares).

Finally.

DESCRIPTION OF PREFERRED EMBODIMENTS

A number of preferred embodiments of the invention, were performed in order to demonstrate that treatment with fatty acid compositions, comprising at least one of EPA and DHA or any combinations thereof, reduces body weight and/or prevents gain in body weight.

In a first preferred embodiment, the effects of an omega-3 fatty acid composition containing about 20% EPA and 50% DHA (weight ratio), on body weight was studied.

In a second preferred embodiment, the effect of the dose of an omega-3 fatty acid composition, rich in DHA, (herein represented as a fatty acid composition comprising about 20% EPA and 50% DHA) in relation to body weight reduction was studied. In a third embodiment of the invention, potential differences in effects between a DHA-enriched omega-3 product, an EPA-product and plant oils containing omega-6 fatty acids, were studied. In the fourth and fifth embodiment of the invention, potential differences in effect between only a DHA-enriched and EPA-enriched omega-3 product, were studied.

In a sixth embodiment of the invention, the effect of an omega-3 fatty acid composition on prevention of obesity and body weight gain, was studied.

Finally, in the seventh study, weight reduction under the condition of developing obesity and additive effects between calorie restriction and an omega-3 fatty acid composition, were evaluated.

Examples

Experiments Performed on Mice

Seventh different experiments were performed on mice to investigate various treatments for reducing body weight and/or for preventing body weight gain.

In study 1-5 adult male mice (C57BL/6J mouse) were randomly assigned different types of semi synthetic high-fat diets where the fat components in respectively study was modified. In the two last studies adult male mice (C57BL/6J mouse) were randomly assigned to a obesity-promoting HF (high fat) diet (35% wt/wt total lipid content) were the fat components was modified.

Study 1: Weight Reduction

Figure 1A:
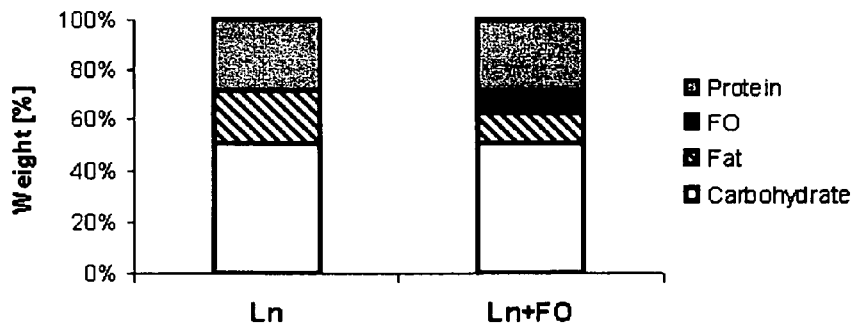
FIG. 1A shows the composition of the semisynthetic high-fat diets (20% w/w fat) containing flaxseed oil with (Ln+FO) respectively without EPAX 2050TG (Ln) given to the different groups of mice's.
Figure 1B:
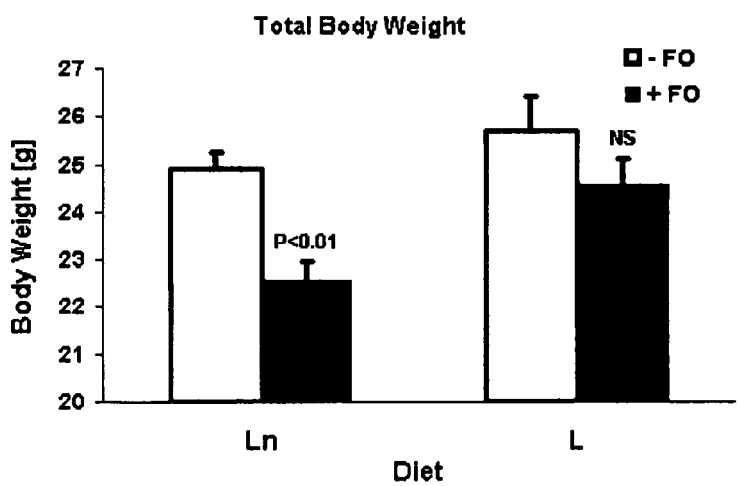
FIG. 1B shows the total body weight after one month of treatment with diets containing flaxseed oil with (Ln+FO) respectively without EPAX 2050TG (Ln) and diets containing lard with (L+FO) respectively without EPAX 2050TG (L).

In the first study, the effects of an omega-3 fatty acid composition containing EPA and DHA on the body weight were studied. A mixture containing approximately 20% EPA and 50% DHA was used. Groups (n=7) of adult male mice (C57BL/6J mouse) fed standard feeding diet (4% fat), were randomly assigned one of four different types of semi synthetic high-fat (20% fat) diets where the fat component was: Group 1) Lard (L), Group 2) Lard plus EPAX2050TG (L+FO: EPAX 2050TG formed 44% w/w of total lipid content), Group 3) Flaxseed oil (18:3n-3 forms about 50% of total lipids; Ln) and Group 4) Flaxseed plus EPAX2050TG (Ln+FO; EPAX 2050TG formed 44% w/w of total lipid content). Note that FO herein means various EPA and DHA concentrates (for instance EPAX high in DHA versus EPAX high in EPA) used in these studies. The animals were fed the different diets mentioned above during 1 month and the composition of the feeding containing flaxseed oil with (Ln+FO) or without EPAX2050TG (Ln) is shown in FIG. 1A. After the study, the total body weight was reduced in Group 2 (L+FO) vs. Group 1 (L); and Group 4 (Ln+FO) vs. Group 3 (Ln), and the difference was statistically significant in Group 4 vs. 3, as evident from FIG. 1B. The body weights of mice before treatment were similar in all the groups. The mice's given flaxseed oil plus EPAX2050TG had decreased by about 10% in body weight compared to the mice's only given flaxseed oil.

This study shows that treatment with a fatty acid composition containing EPA and DHA, wherein the amount of DHA≥EPA, leads to weight reduction.

Study 2: Weight Reduction

Figure 2A:
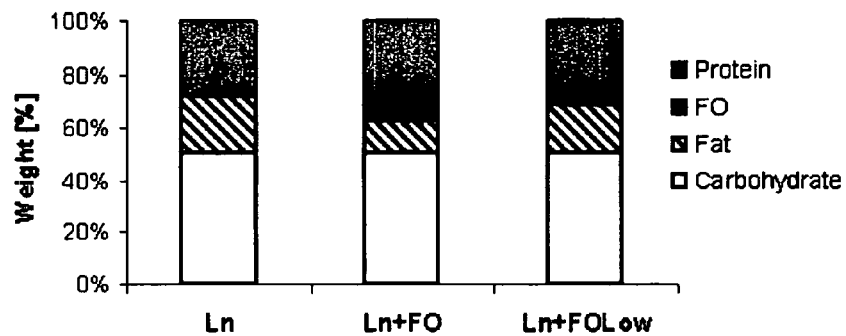
FIG. 2A shows the composition of semi synthetic high-fat diets (20% w/w fat) containing flaxseed oil (Ln), flaxseed oil with a higher dose of EPAX2050TG (Ln+FO) and flaxseed oil with a low dose of EPAX2050TG (Ln+FO Low), given to the different groups of mice.
Figure 2B:
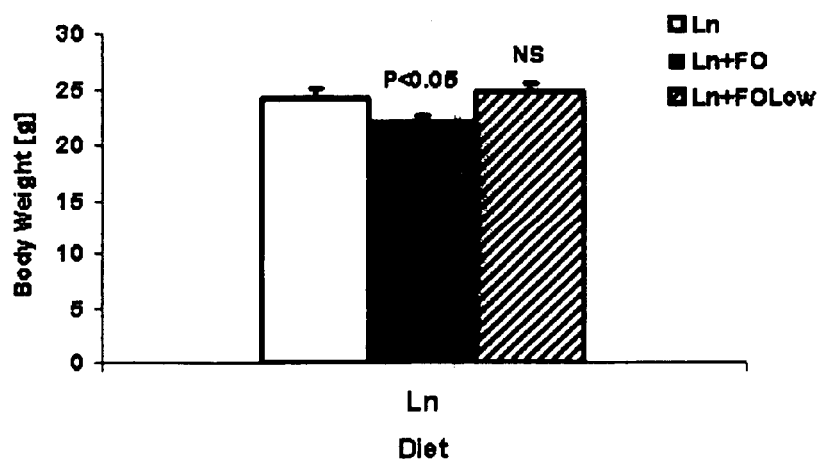
FIG. 2B shows the total body weight after two months of treatment.

In the second study the effect of the dose of an omega-3 fatty acid composition comprising a combination of EPA and DHA (approximately 20% EPA and 50% DHA) in relation to reduction on body weight was studied. Groups (n=7) of adult male mice by standard chow diet (4% fat), were randomly assigned one of three different semi synthetic high-fat (20% fat), for two months. In this experiment group 1) was given Flaxseed oil (Ln), Group 2) Flaxseed oil plus a higher dose of EPAX2050TG (Ln+FO; EPAX2050TG formed 44% w/w of total lipid content), and Group 3) Flaxseed oil plus a lower dose of EPAX2050TG (Ln+FO Low; EPAX 2050TG formed 15% w/w of total lipid content), as the fat component herein. The composition of the diets containing only flaxseed oil (Ln) and flaxseed oil with a higher (Ln+FO) respectively a lower (Ln+FO Low) dose of EPAX2050TG is shown in FIG. 2A. At the end of the study the total body weight was reduced only in group 2, the group given flaxseed oil with a higher dose of EPAX2050TG, as evident from FIG. 2B.

The results of the second study are consistent with the first one, with weight reduction in the group given a fatty acid composition wherein the weight ratio of DHA≥EPA. Moreover, the results from the present study also shows that administration of a fatty acid composition rich in DHA in very low doses did not resulting significant decrease of body weight in rats fed a high fat diet.

Study 3: Weight Reduction

Figure 3A:
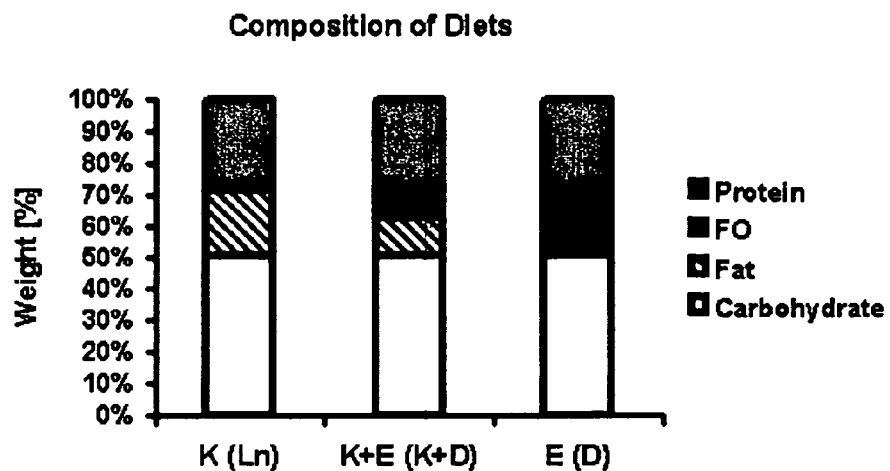
FIGS. 3A and 3B show the composition (in % w/w) of semi synthetic high fat (20% fat) diets containing flaxseed oil (Ln), corn oil (K), EPAX 1050TG (high in DHA) (D), EPAX 4510TG (high in EPA) (E), corn oil+EPAX 1050TG (K+D), and corn oil+EPAX 4510 (K+E), respectively the composition (in % of total energy content of the diet) of standard diet (ST) and semisynthetic diet, given to the different groups of mice's.
Figure 3B:
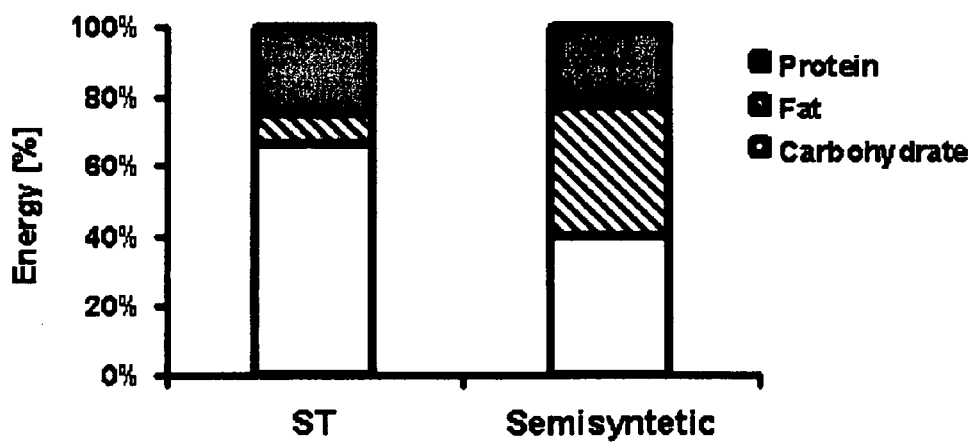
Figure 3C:
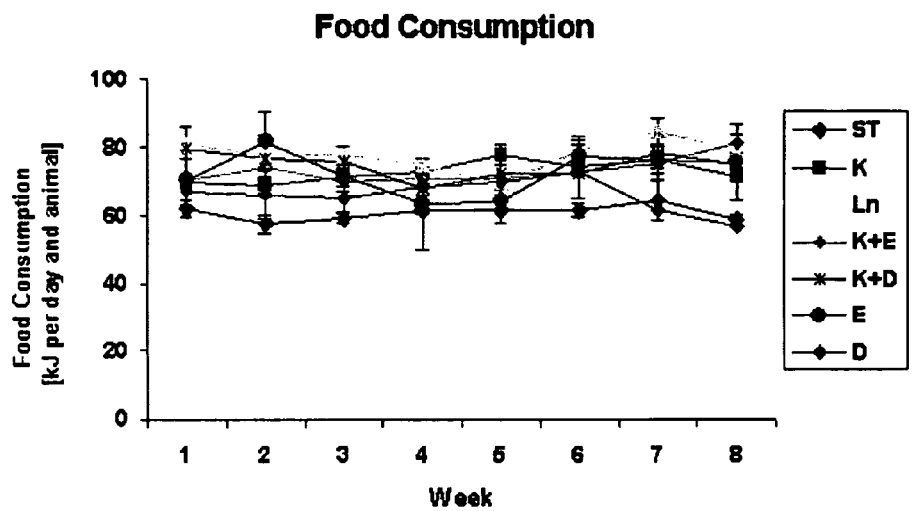
FIG. 3C illustrates the food consumption per day and animal during 8 weeks of treatment.
Figure 3D:
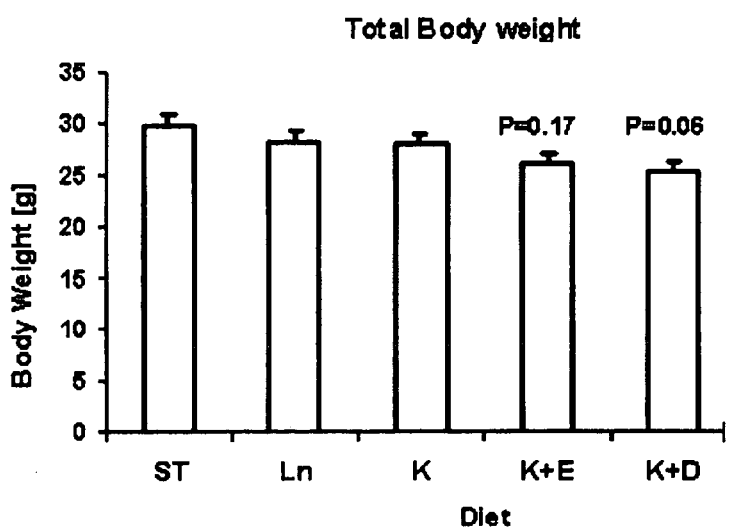
FIG. 3D shows the total body weight after two months of treatment compared to the control group (ST).

In this study potential differences in effects between a DHA-enriched omega-3 product (herein presented as a fatty acid composition comprising approximately 10% EPA and 50% DHA (EPAX1050TG concentrate), an EPA product (rich in EPA, herein presented as a fatty acid composition comprising about 45% EPA and 10% DHA; EPAX4510TG) and plant oils containing omega-6 fatty acids, were studied. Groups (n=7) of adult male mice (C57BL/6J mouse), fed standard chow diet (4% fat), were randomly assigned one of six different types of semisynthetic high-fat (20% fat) diets where the fat component was: group 1) Flaxseed oil (plant omega-3) (Ln), group 2) Corn oil (plant omega-6) (K), group 3) EPAX 1050 (high in DHA) (D), group 4) EPAX 4510TG (high in EPA) (E), group 5) Corn oil+EPAX 1005TG (K+D), and group 6) Corn oil+EPAX 4510TG (K+E). One control group maintained on standard diet (−ST) was also included. The animals were fed the different diets during 2 months. The composition of diets are shown in FIGS. 3A and 3B. As can be seen in FIG. 3C, the food consumption was about 70 KJ per day and animal during the 8 weeks of treatment. The results in FIG. 3D show that treatment with a fatty acid composition containing at least EPA and DHA or combinations thereof leads to weight reduction. Weight reduction has been obtained in animals fed EPAX 1050TG (a fatty acid composition rich in DHA) but less with EPAX 4510TG (a fatty acid composition rich in EPA) in addition (44% of total fat content formed by the product) to corn oil. However, the effect of EPAX 1050TG (high in DHA) was stronger compared with EPAXTG 4510. Moreover, the body weights of the mice fed corn oil plus EPAX 1050TG (high in DHA) had decreased by about 15% in weight. The animals do not tolerate high-fat (20%) semisynthetic diet containing only EPAX 1050TG (high in DHA) as the only lipid constituent. Only 1 out of 7 mice fed EPAX 1050TG survived longer than 4 weeks on the diet. The mice's got to slimy. All of the mice fed only EPAX 4510TG containing diet survived but looked unhealthy.

The results of the third study shows that the weight lowering effect of a fatty acid composition comprising about 10% EPA and 50% DHA (a fatty acid composition rich in DHA), was stronger compared to a fatty acid composition comprising about 45% EPA and 10% DHA (rich in EPA). Furthermore, weight reduction due to corn oil was similar to the reduction due to a fatty acid composition comprising about 20% EPA and 50% DHA in flaxseed oil (in the 1$^{st}$ and the 2$^{nd}$ experiment) and stronger than the reduction due to a fatty acid composition comprising about 20% EPA and 50% DHA in lard (in the 1$^{st}$ experiment) Once more above states a best mode using a product rich in DHA, preferably DHA≥EPA. These results also suggest a specific weight-lowering effect of an omega-3 product of marine origin as compared with plant oils (both omega-3 and omega-6) and saturated fats (lard).

Study 4: Effects of a Fatty Acid Composition Rich in EPA Versus a Fatty Acid Composition Rich in DHA on Weight Reduction In this study, potential differences in effects between a DHA-enriched omega-3 product (herein presented as a fatty acid composition comprising approximately 10% EPA and 50% DHA (EPAX1050TG concentrate)) and an EPA product (rich in EPA, herein presented as a fatty acid composition comprising about 45% EPA and 10% DHA; EPAX4510TG) were studied. At four months of age, chow diet-fed mice were divided into 2 groups (n=7) and fed semi-synthetic HFs diet based on corn oil (20% wt/wt total lipid content) either with replacement of 44% (wt/wt) of its fat content by EPAX 4510TG (rich in EPA) or EPAX 1050TG (rich in DHA). After two months on the respective diets, the addition of both types of omega-3 PUFA products to the diet resulted in a reduction of body weight, see table 1 below.

TABLE 1

Effects of omega-3 PUFA on body weight in mice fed semi-synthetic HF diet based on corn oil.

| Body weight (g) | Replacement of 44% (wt/wt) of the diets fat content by EPAX 4510TG (rich in EPA) | Replacement of 44% (wt/wt) of the diets fat content by EPAX 1050TG (rich in DHA) |
|---|---|---|
| Initial | 27.1 ± 0.6 | 27.2 ± 0.5 |
| Final | 26.2 ± 0.7 | 25.4 ± 0.7 |
| Change | −0.7 ± 0.6$^b$ | −1.4 ± 0.4b |

$^b$Statistically significant differences compared to HF.

However, the DHA rich product EPAX 1050TG exhibited stronger effect compared to EPAX 4510TG on weight reduction. Additionally, the results of this study confirm significant effects supporting the weight-reducing effect influenced of a EPAX rich in DHA.

Figure 4:
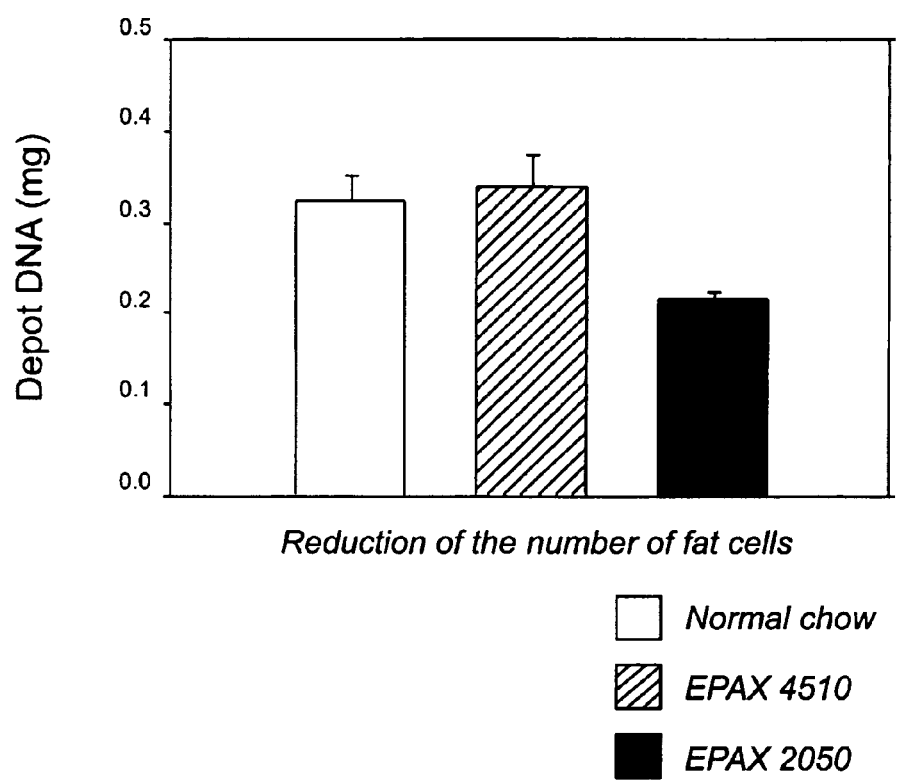
FIG. 4 shows a reduction of DNA. Moreover.

Study 5: Effects of a Fatty Acid Composition Rich in EPA Versus a Fatty Acid Composition Rich in DHA on Reduction in DNA In this study, further potential differences in effects between a DHA-enriched omega-3 product (herein presented as a fatty acid composition comprising approximately 20% EPA and 50% DHA (EPAX1005TG concentrate)) and an EPA product (rich in EPA, herein presented as a fatty acid composition comprising about 45% EPA and 10% DHA; EPAX4510TG) were studied. At four months of age, chow diet-fed mice were divided into 3 groups (n=7) and fed semi-synthetic HFs diet based on flaxseed oil (alpha-linoleic acid constitutes about 50% of total lipids) either with replacement of 30% (wt/wt) of its fat content by EPAX 4510TG (rich in EPA; hatched bars) or EPAX 2050TG (rich in DHA; black bars), or the semi-synthetic HF diet alone (open bars). After one month on the respective diets, DNA was analysed. Addition of the omega-3 PUFA product rich in DHA (EPAX 2050TG) to the diet resulted in a reduction of DNA, which may indicate a reduction of the number of fat cells, see FIG. 4.

Thus, a DHA-concentrate and/or a fatty acid composition rich in DHA according to the invention leads to reduction of DNA, which seems to indicate a reduction of the number of fat cells (i.e. fat cells are killed) in adipose tissue.

Study 6: Prevention of Body Weight Gain and Obesity

Figure 5A:
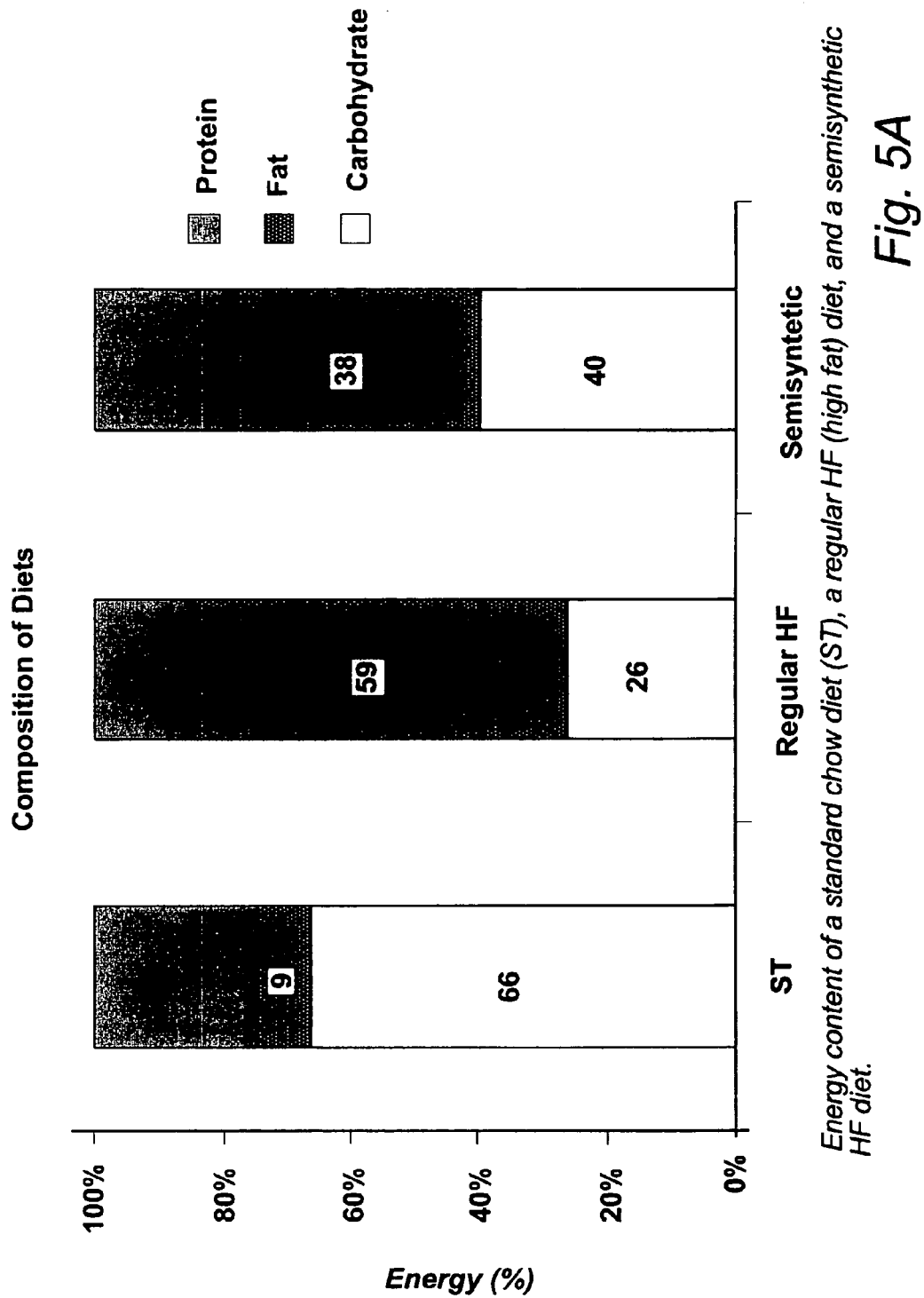
FIG. 5A shows the energy content of a standard chow diet (ST), a regular HF (high fat) diet, so called obesity-promoting diet, and a semi synthetic high fat (20% fat) diet. Moreover.

In this sixth study the effect of an omega-3 fatty acid composition comprising a combination of EPA and DHA (approximately 20% EPA and 50% DHA) on prevention of obesity and gain of weight, was studied. Groups (n=7) of adult C57BL/6J male mice were housed in a controlled environment (200° C., 12-h light-dark cycle, light from 6:00 a.m.) with free access to water and standard chow diet enriched with sunflower oil as the main lipid constituent and containing negligible amounts of LC omega-3 PUFA. At 4 months of age (−2 weeks) the chow diet was replaced by a HF (high-fat) diet or herein a so called obesity-promoting HF diet (35% wt/wt total lipid content), please see FIG. 5A for diet composition. The energy density of the HF composite diet was 22.3 kJ/g. When the mice's were offered the HF (high fat) composite diet they started to gain body weight at a much higher rate than maintained on chow diet. Two weeks later (0 weeks) the animals were divided into 5 subgroups and fed ad libitum HF composite diet, either with no further modification (full circles), or with replacement of 15% (wt/wt; i.e. 9% dietary lipids by EPA+DHA; empty circles) or 44% (wt/wt; i.e. 26% lipids formed by EPA+DHA; full triangles) of its fat content by EPAX 2050TG (rich in DHA), see table 2 below.

| Product | Composition EPA/DHA$^a$ | Content (% lipids)$^b$ | HF composite diet$^c$ - amount EPA | HF composite diet: - amount DHA |
|---|---|---|---|---|
| EPAX 1050TG | 6/51 | 15 | 0.33 | 2.80 |
| EPAX 1050TG | 6/51 | 44 | 0.97 | 8.26 |

$^a$Amounts of EPA and DHA in different products are expressed as g EPA/g DHA in 100 g of the product
$^b$Percentage (wt/wt) of the lipid components in the diet replaced by omega-3 PUFA product
$^c$HF composite diet (35% wt/wt total lipid content) and a portion of the lipid component was replaced by EPAX1050 products Mice on the Calorie Restriction (CR) regime (30% calorie restriction when compared with ad libitum fed maice on the same diet) were fed either the HF composite diet alone (empty triangles) or the diet, in which 15% (wt/wt) of the lipids in the diet was formed by EPAX 1050TG (i.e. about 3 out of 35 g of the lipids in each 100 g of the diet, about 9% of lipids, were replaced by EPA/DHA; full squares).

Figure 5C:
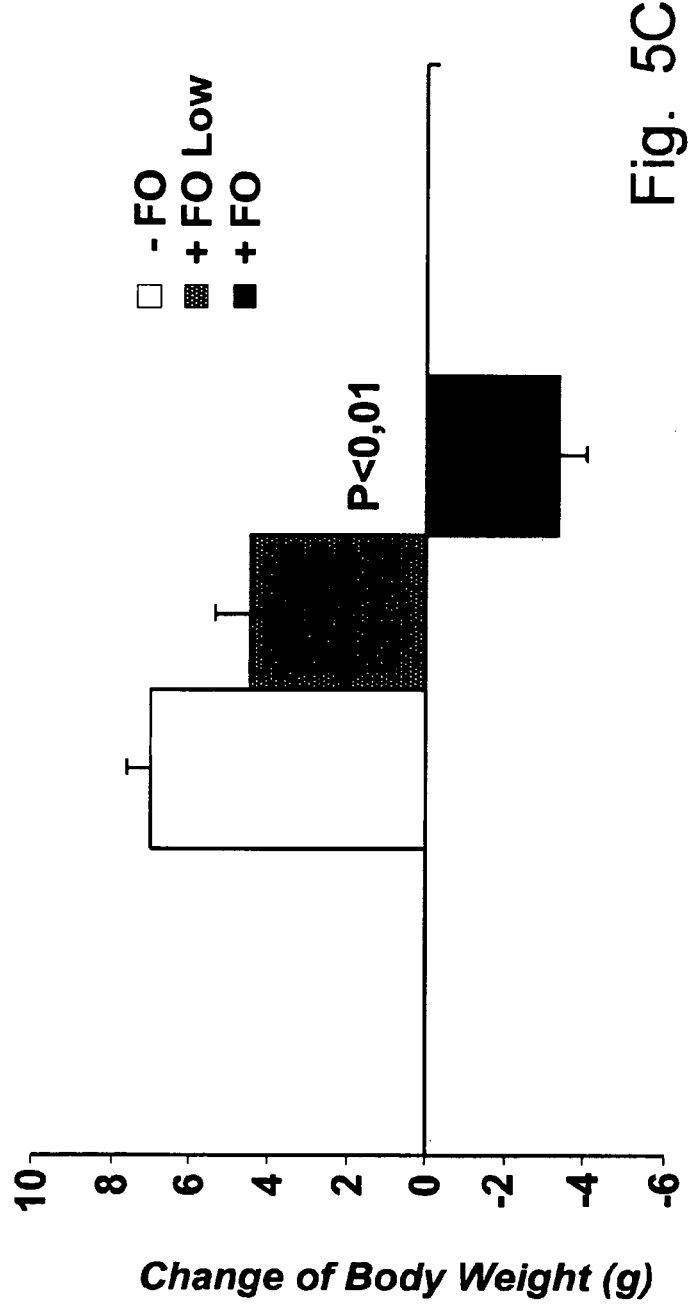
FIG. 5C illustrates a dose-dependent effect of omega-3 products added to regular HF obesity-promoting diet and under the condition of development of obesity.

The results of this study are shown in FIG. 5B. Weight gain was apparent after about 2 weeks of habituation on the HF diet and reached about 6.5 g within the next 5 weeks of the experiment. Body weight gain was about 2.7 g lower in mice fed a HF composite diet where 15% lipids in the diet were replaced by omega-3 product EPAX 1050 TG (rich in DHA)

compared to mice fed only the HF composite diet. This states that even a low dose of omega-3 product (only 15% w/w of the fat content of the diet) slowed down the development of obesity in ad libitum fed mice. Replacement of 44% of the lipids by the EPAX1050 TG resulted in a net loss of body weight of about 3 g over 5-weeks feeding period. Under these conditions the omega-3 group lost body weight during the 5-week treatment while the control group (regular HF diet) gained body weight. The above indicates a dose-dependent effect of the omega-3 product added to regular HF obesity-promoting diet, and under the condition of development of obesity even a low dose of a fatty acid composition rich in DHA reduced gain in body weight already after 5 weeks of treatment. Please also se a summary in FIG. 5C.

As is also be apparently from the study, 30% calorie restriction in animals fed HF composite diet resulted in a net loss of body weight during 5 weeks of treatment while admixing EPAX 1050 in the diet of the CR-animals only has a small extensive effect on weight loss, i.e. a additive effect on body weight reduction, compared to animals on 30% CR. Therefore, the interaction between CR and omega-3 products will be investigated more in detail in a further study. Please also note that replacement of dietary lipids by the omega-3-product seams not to affect food consumption of the animals. Moreover, the results from this study show that administration of a fatty acid composition rich in DHA in low doses results in significant inhibition or prevention of weight gain. A fatty acid composition rich in DHA in a higher dose shows both significant inhibition or prevention of weight gain and a weight-lowering effect under the conditions of developing obesity. Thus the dose of EPAX 1050 TG required to counteract the increase in body weight in the context of dietary obesity is lower than that required to reduce body weight in animals maintaining relatively stable body weight on the HF semi-synthetic diet. Apparently, development of obesity makes the organism more sensitive to the weight-reducing effect of the fatty acid composition comprising EPA and DHA. Additionally, the experiment described above demonstrates significant reduction of obesity in mice fed HF composite diet containing long chain omega-3 fatty acids. This study shows that treatment of obese, or overweight animals with a fatty acid composition containing EPA and DHA, wherein the amount of DHA≥EPA, also leads to prevention of weight gain. The effect of preventing body weight gain also means prevention of obesity or an overweight condition.

Study 7: Weight Reduction Under the Condition of Developing Obesity, and Additive Effect of Calorie Restriction (CR) and an omega-3 Fatty Acid Composition In the previous study, the effect of calorie restriction and a fatty acid composition rich in DHA on weight reduction under the condition of developing obesity was not fully evaluated. Therefore, a complementary study on the interaction between calorie restriction and omega-3 products, herein presented as a DHA-enrich omega-3 product comprising approximately 10% EPA and 50% DHA (EPAX1050TG), during development of obesity in mice was performed. Group of C57BL/6J male mice (n=7) were housed in a controlled environment (20° C., 12-h light-dark cycle, light from 6:00 a.m.) with free access to water and standard chow diet. At 4 months of age, the animals were randomly assigned to a obesity-promoting HF (high-fat) diet, please see FIG. 4A for diet composition. Two weeks later (week 0) after habituation on the diet mentioned above, the animals were divided into 4 groups: a) HF composite diet ad libitum; b) HF composite diet with 10% calorie restriction compared to (a); c) fed ad libitum by HF composite diet where 15% of the fat content of the diet was replaced by EPAX1050TG; and d) fed ad libitum HF composite diet where 15% of the fat content of the diet was replaced by EPAX1050TG and the amount of food was restricted by 10% compared to (a). The animals were fed the different diets during 5 weeks.

Figure 6:
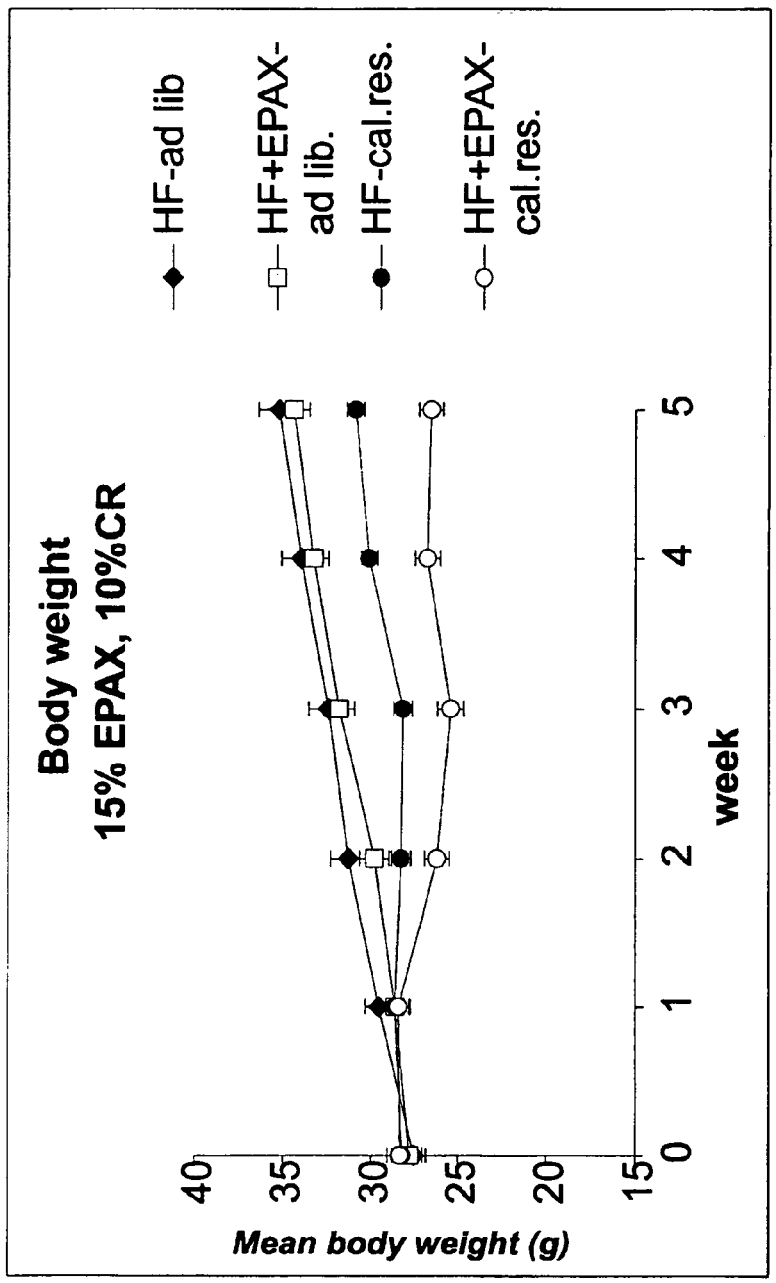
FIG. 6 shows the effects of EPAX 1050TG and 10% calorie restriction on body weight.

The results in FIG. 6 show that treatment under conditions of developing obesity with a fatty acid composition containing at least one of EPA and DHA or combinations thereof, significantly decreases the gain in body weight in relation to mice only fed obesity-promoting HF diet. In contrast to the previous study, the mild calorie restriction reduced development of obesity. Herein the difference between HF-ad libit and HF+EPAX-ad lib is statistically significant (paired t-test, P≤0.03). Moreover, the combination of the two treatments, i.e. were 10% of the amount of food was restricted and 15% of the fat content of the diet was replaced by EPAX1050TG, has an additive effect resulting in prevention of the body weight gain as compared to the control HF diet fed mice.

The results in the seventh study show that a fatty acid composition rich in DHA enhances the effect of calorie restriction (CR) on developing obesity in animals fed HF composite diet, i.e. under the conditions closely mimicing obesity in humans consuming excessive amounts of high fat containing diet. High food intake renders an animal or a human more sensitive to the effect of fatty acid composition comprising at least one of EPA and DHA or combinations thereof, and seems to be necessary for the additive effect concerning prevention of body weight gain of a fatty acid composition comprising at least one of EPA and DHA, or combinations thereof and calorie restriction to occur. This states that a fatty acid composition comprising at least one of EPA and DHA, or any combinations thereof, not only reduces body weight but may also prevent gain of weight and obesity. Once again a best mode according to the invention may be achieved by using a product rich DHA, preferably DHA≥EPA. Additionally, these results also open up for a more manageable dietary regime of calorie restriction for a human since the result show an effect already at low levels of calorie restriction.

Doses of the Fatty Acid Composition

Concerning the dose, the results from mice may be extrapolated to humans, as far as the relative content of the fatty acid composition according to the invention, for instance an fatty acid composition containing EPA and DHA or any combinations thereof, in the diet is concerned. In the studies before, a semi-synthetic diet containing 20% (w/w) fat was used, and an effect on weight reduction was observed when at least about 28% of the lipid content was replaced by a fatty acid composition according to the invention (by the addition of a fatty acid composition according to the invention), while there was almost no effect on weight reduction when a fatty acid composition according to the invention formed 9% of the lipid content of the diet. These diets provided 40% of the energy from lipids.

The relative content of the fatty acid composition according to the invention with respect to the total lipid content (in the diet) may be more important than the absolute intake, as far as the effect on weight reduction is concerned. Therefore, one embodiment of the invention is to replace at least ⅓ of the total lipid in the diet by a fatty acid composition comprising at least one of DHA and EPA or any combinations thereof, according to the invention. Please see some relevant fictive scenarios presented below.

1. A human on a low calorie diet consume, 1000 kcal/day with 18% calories from fat. In order to replace 28% of 20 g of the a total lipid intake by a fatty acid composition according to the invention, the person need 5.6 g fatty acid composition/day.

By assumed synergism between calorie restriction and the fatty acid composition according to the invention in the effect on weight reduction, also lower concentrations of the fatty acid composition in dietary lipids show effect on weight reduction.

In another preferred embodiment of the invention, at least 15% of the lipid content in the diet is replaced by the fatty acid composition according to the invention. This means about 3 g of the fatty acid composition per day, in a very low calorie diet of 1000 kcal/day with 18% calories from fat.

In a preferred embodiment of the invention, the treatment and/or prevention of obesity or overweight conditions, or for weight control and/or for prevention of body weight gain according to the invention, is carried out together with a reduced intake of calories for a human or an animal. Preferably, the dietary regime of calorie reduction is combined with physical activity.

In another preferred embodiment of the invention, said reduced intake of calories is reduced to at least 800 kcal (2520 KJ per day) or less, for a short and drastic treatment of obese patients (adult persons). In a more preferred embodiment, said fatty acid composition comprising at least one of EPA, derivatives thereof, and DHA, or any derivatives thereof, or any combinations thereof, is administered in a daily dosage from (corresponding to) 10 up to 40% of the total lipid content of a daily diet for a human. Moreover, to achieve a improved result, the lipid content of the diet may be lowered to at least 15% of its energy content. The fatty acid composition according to the invention is preferably administered daily, divided in dosage, for periods up to 1-5 years. On the other hand, the dosage of the fatty acid composition according to the invention may also be related to the amount of omega-3 fatty acids consumed by for instance Eskymo's or similar native people. Therefore, in an another embodiment of the invention said fatty acid composition comprising at least one of EPA and DHA, or derivatives thereof, or any combinations thereof, is administered in an amount providing a daily dosage of 1 g to 15 g of said fatty acid composition. More preferred in an amount of 1 to 10 g, and most preferred an amount of between 2 and 6 g per day.

Discussion

The results shows that a fatty acid composition comprising at least one of EPA and DHA or any combinations thereof, reduce body weight and/or prevent body weight gain. The weight lowering effect of a product according to the invention that is rich in DHA is stronger compared to a product containing more EPA than DHA. Moreover, preferably a specific weight-lowering effect and prevention of body weight gain is achieved of a fatty acid composition according to the invention of marine origin. Further, based on the results, calculations of doses and commercial value, the use of the fatty acid composition according to the present invention preferably may go hand-in-hand with a dietary regimen of calorie reduction. Moreover, an additive effect of a fatty acid composition according to the invention combined with calorie restriction is achieved under conditions of high food intake and development of an overweight condition or obesity. It is also obvious to expect the same weight lowering effect and/or prevention of body weight gain on both humans and animals by administering the fatty acid composition according to the invention.

Additionally, a DHA-concentrate and/or a fatty acid composition rich in DHA according to the invention may reduce the number of fat cells in adipose tissue.

Reduction of body weight and/or prevention of body weight gain due to administration of a fatty acid composition according to the invention, preferably a fatty acid composition rich in DHA, may result, at least in part, from increased oxidation of lipids (fatty acids) inside adipose tissue cells in a human or an animal. Thus, a fatty acid composition, preferably rich in DHA, induces metabolic switch in adipocytes (fat cells) that seem to prevent accumulation of body fat. The switch may be activated by direct interaction of a fatty acid composition according to the invention, preferably a fatty acid composition rich in DHA, with adipocytes through induction of genes controlling oxidative capacity of mitochondria. Transcriptional factors orchestrating mitochondrial biogenesis (PGC1 and NRF1) seem to be involved. Changes in gene expression seem to result in increased content of mitochondrial components which are critical for oxidation of various substrates, including lipids, in adipocytes. Further, a fatty acid according to the invention may increase the ratio between the activities of fatty acid oxidation and synthesis in adipose tissue, thus activating a metabolic switch.

The invention shall not be limited to the shown embodiments and examples.

The invention claimed is:

1. A method for at least one of treatment of obesity, prevention of obesity, treatment of an overweight condition, prevention of an overweight condition, controlling body weight reduction, and prevention of body weight gain, comprising:
    administering an effective amount of a fatty acid composition comprising at least one of (all-Z omega-3)-5,8,11,14,17-eicosapentaenoic acid (EPA), or derivatives thereof, and (all-Z omega-3)-4,7,10,13,16,19-docosahexaenoic acid (DHA), or derivatives thereof, or any combinations thereof, to at least one of a human and an animal, wherein the weight ratio of EPA:DHA in the fatty acid composition is 1:X, where X is greater than 1; wherein the concentration of EPA ranges from 10% to 20% and the concentration of DHA ranges from 20% to 50%; wherein the human is an adult.

2. The method according to claim 1, wherein the EPA and DHA are present in the composition in an EPA:DHA ratio ranging no more than 1:8.

3. The method according to claim 1, wherein the fatty acids in the composition are present in at least one of esterified form, ethyl ester form, salt form and free acid form, and any combinations thereof.

4. The method according to claim 1, wherein the fatty acid composition comprises EPA and DHA in triglyceride form.

5. The method according to claim 1, wherein at least one of EPA and DHA is obtained from at least one of vegetable, microbial and animal origin.

6. The method according to claim 1, wherein at least a part of the EPA and/or DHA is obtained from a marine oil.

7. The method according to claim 1, wherein the composition is administered orally to the at least one of a human and an animal.

8. The method according to claim 1, wherein the treatment is carried out together with a reduced intake of calories for the at least one of a human and an animal.

9. The method according to claim 1, wherein said fatty acid composition is administered in a daily dosage that corresponds to at least 10% of the total lipid content of a daily diet for the at least one of a human and an animal.

10. A method for supplementing a dietary product comprising:
    adding a fatty acid composition comprising at least one of (all-Z omega-3)5,8,11,14,17-eicosapentaenoic acid (EPA), or derivatives thereof, and (all-Z omega-3)4,7,10,13,16,19-docosahexaenoic acid (DHA), or derivatives thereof, or any combinations thereof, to supplement the dietary product for at least one of prevention of body weight gain and controlling and supporting weight reduction in a human, wherein the weight ratio of EPA:DHA in the fatty add composition is 1:X, where X is larger than 1;

wherein the concentration of EPA ranges from 10% to 20% and the concentration of DHA ranges from 20% to 50%;

wherein the human is an adult.

11. The method according to claim 10, wherein the fatty acid composition is present in at least one of liquid form and as an emulsion, being incorporated in said dietary product.

12. The method according to claim 10, wherein said fatty acid composition is chosen from a supplement, a food supplement, and a nutritional product.

13. A method for at least one of treatment of obesity, prevention of obesity, treatment of an overweight condition, prevention of an overweight condition, controlling body weight reduction, and prevention of body weight gain, comprising:

administering an effective amount of a fatty acid composition comprising at least one of (all-Z omega-3)-5,8,11,14,17-eicosapentaenoic acid (EPA), or derivatives thereof, and (all-Z omega-3)-4,7,10,13,16,19-docosahexaenoic acid (DHA), or derivatives thereof, or any combinations thereof, to at least one of a human and an animal, wherein the concentration of EPA ranges from 10% to 20% and the concentration of DHA ranges from 20% to 50% and the concentration of DHA is greater than the concentration of EPA;

wherein the human is an adult.

14. The method according to claim 13, wherein the concentration of EPA is 10% and the concentration of DHA is 50%.

15. The method according to claim 13, wherein the concentration of EPA is 20% and the concentration of DHA is 50%.

16. The method according to claim 1, wherein the concentration of EP is 10% and the concentration of DHA is 50%.

17. The method according to claim 1, wherein the concentration of EPA is 20% and the concentration of DHA is 50%.

18. The method according to claim 10, wherein the concentration of EP is 10% and the concentration of DHA is 50%.

19. The method according to claim 10, wherein the concentration of EPA is 20% and the concentration of DHA is 50%.

* * * * *